United States Patent
Usui et al.

(10) Patent No.: US 10,444,197 B2
(45) Date of Patent: Oct. 15, 2019

(54) DETECTION SYSTEM AND DETECTION METHOD

(71) Applicant: Kabushiki Kaisha Toshiba, Tokyo (JP)

(72) Inventors: Takashi Usui, Saitama (JP); Kazuo Watabe, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 16/163,706

(22) Filed: Oct. 18, 2018

(65) Prior Publication Data

US 2019/0064118 A1 Feb. 28, 2019

Related U.S. Application Data

(63) Continuation of application No. 15/070,981, filed on Mar. 15, 2016.

(30) Foreign Application Priority Data

Mar. 23, 2015 (JP) ................................. 2015-059491

(51) Int. Cl.
  *G01N 29/32* (2006.01)
  *G01N 29/44* (2006.01)
  *G01N 29/14* (2006.01)

(52) U.S. Cl.
  CPC ............. *G01N 29/14* (2013.01); *G01N 29/32* (2013.01); *G01N 29/4436* (2013.01)

(58) Field of Classification Search
  CPC ..... G01N 29/14; G01N 29/4436; G01N 29/32
  USPC ........................................................ 73/587
  See application file for complete search history.

(56) References Cited

U.S. PATENT DOCUMENTS

| 5,285,688 A | 2/1994 | Robbins et al. |
| 5,681,995 A | 10/1997 | Ooura |
| 5,987,990 A | 11/1999 | Worthington et al. |
| 7,930,175 B2 | 4/2011 | Haulick et al. |
| 8,264,337 B2 | 9/2012 | Handa |
| 2006/0095223 A1 | 5/2006 | Gordon |
| 2006/0106551 A1 | 5/2006 | Morin |
| 2009/0043516 A1 | 2/2009 | Liu |
| 2011/0196622 A1 | 8/2011 | Tsubata |

(Continued)

FOREIGN PATENT DOCUMENTS

| JP | S51-114980 | 10/1976 |
| JP | S55-78250 A | 6/1980 |

(Continued)

*Primary Examiner* — Jacques M Saint Surin
(74) *Attorney, Agent, or Firm* — Finnegan, Henderson, Farabow, Garrett & Dunner, L.L.P.

(57) ABSTRACT

According to an embodiment, a detection system includes a plurality of first sensors, a second sensor, a first calculator, and a second calculator. Each of the first sensors is configured to detect an elastic wave generated from a structure, and convert the elastic wave into a detection signal. The second sensor is configured to detect a noise propagating from surroundings, and convert the noise into a reference signal. The first calculator is configured to calculate a plurality of difference detection signals based on the respective detection signals and the reference signal. The second calculator is configured to calculate a position of a generation source of the elastic wave from the plurality of difference detection signals.

9 Claims, 13 Drawing Sheets

(56) References Cited

U.S. PATENT DOCUMENTS

| | | | | |
|---|---|---|---|---|
| 2016/0139084 A1* | 5/2016 | Usui | ...................... | G01N 29/14 |
| | | | | 73/587 |
| 2017/0336365 A1* | 11/2017 | Watabe | ............... | G01M 5/0008 |
| 2018/0074019 A1* | 3/2018 | Iida | ........................ | G01N 29/07 |
| 2018/0074023 A1* | 3/2018 | Iida | ........................ | G01N 29/14 |

FOREIGN PATENT DOCUMENTS

| JP | S61-117449 A | | 6/1986 | | |
|---|---|---|---|---|---|
| JP | H6-18491 A | | 1/1994 | | |
| JP | 08286818 A | * | 11/1996 | ............... | G06F 3/03 |
| JP | 2003-156412 A | | 5/2003 | | |
| JP | 2006-58278 A | | 3/2006 | | |
| JP | 2008-22534 A | | 1/2008 | | |
| JP | 2008-26070 A | | 2/2008 | | |
| JP | 2010-14624 A | | 1/2010 | | |
| JP | 2012-42440 A | | 3/2012 | | |
| JP | 2012-251391 A | | 12/2012 | | |
| JP | 2016-99119 A | | 5/2016 | | |

* cited by examiner

| QUALITY OF MATERIAL | PROPAGATION SPEED v [m/s] |
|---|---|
| IRON | 5950 |
| CONCRETE 1 | 4570 |
| CONCRETE 2 | 3660 |

DETECTION SYSTEM AND DETECTION METHOD

CROSS-REFERENCE TO RELATED APPLICATION

This application is a Continuation of U.S. application Ser. No. 15/070,981, filed Mar. 15, 2016, which is based upon and claims the benefit of priority from Japanese Patent Application No. 2015-059491, filed on Mar. 23, 2015; the entire contents of which are incorporated herein by reference.

FIELD

Embodiments described herein relate generally to a detection system and a detection method.

BACKGROUND

In recent years, problems associated with aging of structures such as bridges built during the period of rapid economic growth become actualized. Damages of if accidents occur in the structures are incalculable. Therefore, technologies for monitoring states of the structures are known. For example, technologies for detecting damage of the structures by an acoustic emission (AE) system that detects elastic waves generated in association with generation of internal cracks or development of the internal cracks by high-sensitive sensors are known.

The acoustic emission is an elastic wave generated in association with development of fatigue cracks of material. In the AE system, this elastic wave is detected by an AE sensor using a piezoelectric element as a voltage signal (AE signal). The AE signal is detected as a premonition before rupture of the material is caused, and thus the frequency of generation of the AE signal and signal intensity of the AE signal are useful as indexes that indicate soundness of the material. Therefore, technologies for detecting an indication of deterioration of structures by the AE system have been actively studied. Especially, in corrosion diagnosis of oil tanks, manufacturing processes of mechanical devices, and the like, the detection technologies of the AE system have been widely used mainly in Europe and the United States, and standardization of the detection technologies of the AE system has been performed.

The AE signal is typically a feeble signal and a signal level thereof needs to be increased using an amplifier having high degree of amplification, and thus the AE signal is susceptible to noises while being highly sensitive. Therefore, in conventional technologies, the noises that are significant enough to cause erroneous determination of AE signal detection may be superimposed depending on an AE signal detection environment.

DETAILED DESCRIPTION

According to an embodiment, a detection system includes a plurality of first sensors, a second sensor, a first calculator, and a second calculator. Each of the first sensors is configured to detect an elastic wave generated from a structure, and convert the elastic wave into a detection signal. The second sensor is configured to detect a noise propagating from surroundings, and convert the noise into a reference signal. The first calculator is configured to calculate a plurality of difference detection signals based on the respective detection signals and the reference signal. The second calculator is configured to calculate a position of a generation source of the elastic wave from the plurality of difference detection signals.

Hereinafter, embodiments of a detection system and a detection method will be described in detail with reference to the appended drawings.

Figure 1:
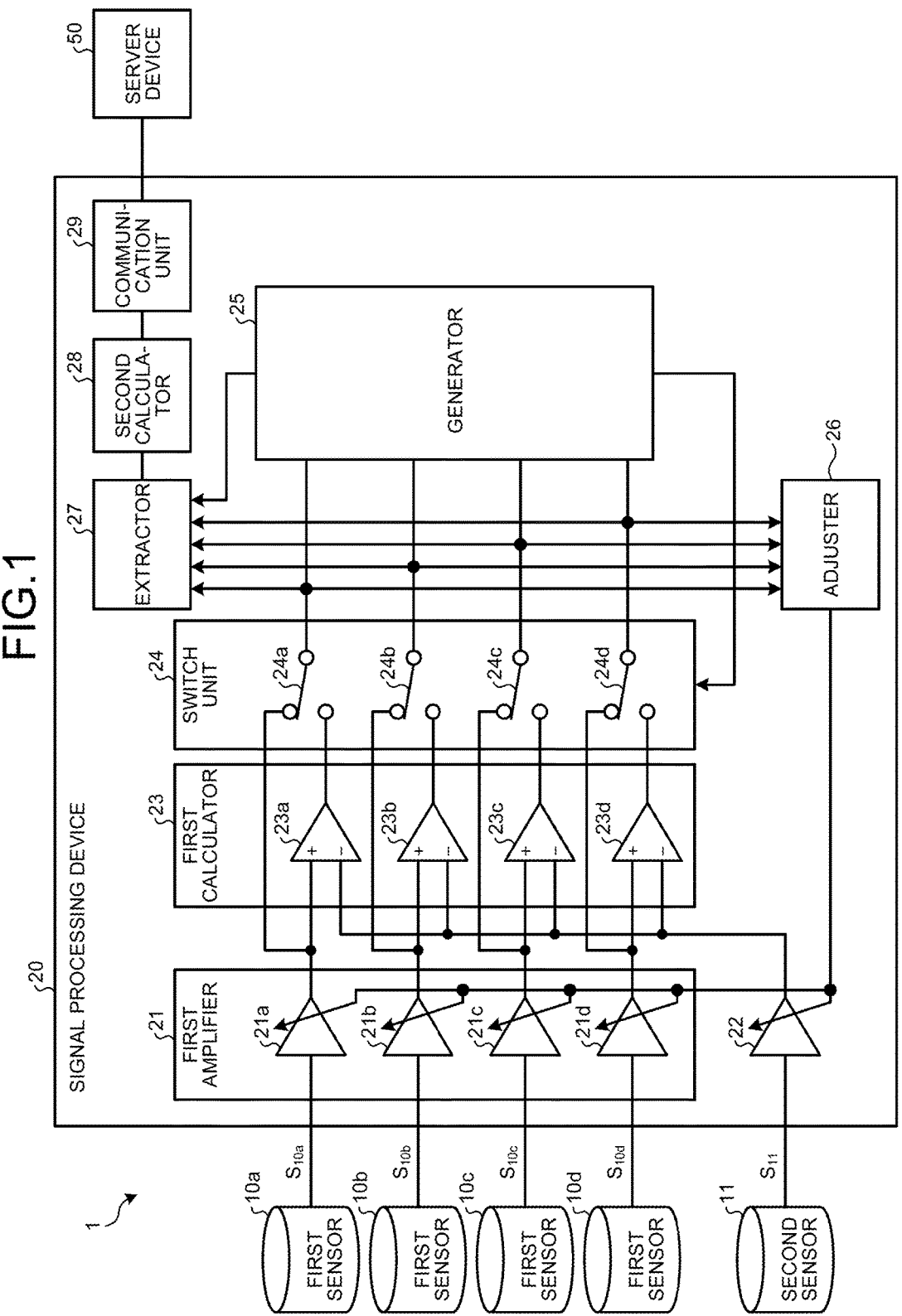
FIG. 1 is a diagram illustrating an example of a configuration of a detection system of an embodiment.

FIG. 1 is a diagram illustrating an example of a configuration of a detection system 1 of an embodiment. The detection system 1 of an embodiment includes first sensors 10a to 10d, a second sensor 11, and a signal processing device 20.

The first sensors 10a to 10d and the second sensor 11 are installed in a structure such as a bridge. The first sensors 10a to 10d detect an elastic wave (an AE wave) generated from the structure, and convert the elastic wave into electrical signals such as voltage signals. Hereinafter, these electrical signals are referred to as detection signals. Further, when the first sensors 10a to 10d are not distinguished, they are simply called first sensor 10.

Meanwhile, the second sensor 11 detects noises (electrical noises) propagating from surroundings of the second sensor 11, and converts the noises into an electrical signal such as a voltage signal. Hereinafter, this electrical signal is referred to as reference signal. Here, the noises will be described.

Figure 2:
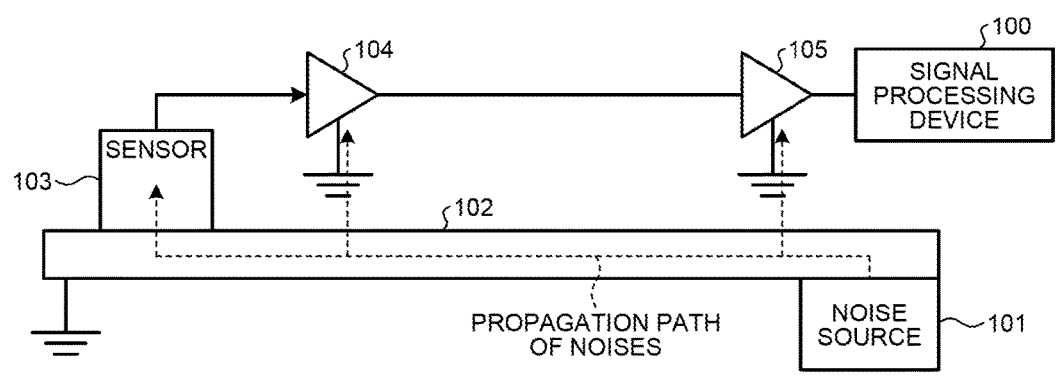
FIG. 2 is a diagram for describing a first example of a typical approach path of noises.

FIG. 2 is a diagram for describing a first example of a typical approach path of noises. The example of FIG. 2 illustrates a case of a signal processing device 100 that receives a signal from a sensor 103 installed in a metal 102 through an amplifier 104 and an amplifier 105. A noise source 101 is, for example, a separate device (circuit) from the signal processing device 100. The noises approach the sensor 103 from the noise source 101 through the metal 102, and the noises approach the signal processing device 100 through the amplifiers 104 and 105. Further, the noises approach the signal processing device 100 from a ground of the amplifier 104 and a ground of the amplifier 105 through the metal 102.

Figure 3:
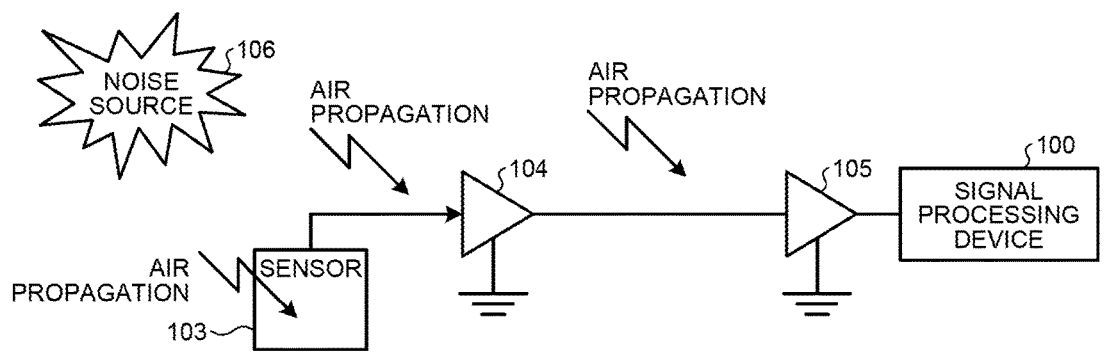
FIG. 3 is a diagram for describing a second example of the typical approach path of noises.

FIG. 3 is a diagram for describing a second example of a typical approach path of noises. The example of FIG. 3 illustrates a case of the signal processing device 100 that receives a signal from the sensor 103 through the amplifiers 104 and 105. A noise source 106 is an electromagnetic wave emitted from a separate device from the signal processing device 100. The noises propagates in the air from the noise source 106 to the sensor 103, and to a signal line between the sensor 103 and the signal processing device 100, thereby to approach the signal processing device 100.

Referring pack to FIG. 1, piezoelectric elements having sensitivity in a range from 10 kHz to 1 MHz are used for the first sensor 10 and the second sensor 11. Examples of types of the first sensor 10 and the second sensor 11 include a resonance type having a resonance peak in a frequency range, a broadband type that suppresses resonance, or the like. The first sensor 10 and the second sensor 11 may employ any type. Further, the first sensor 10 and the second sensor 11 may have a pre-amplifier built-in. Further, examples of a detection method by the first sensor 10 and the second sensor 11 include a voltage output type, a resistance change type, and an electrostatic capacity type, and the like. Any detection method may be employed.

The signal processing device 20 of an embodiment includes a first amplifier 21, a second amplifier 22, a first calculator 23, a switch unit 24, a generator 25, an adjuster 26, an extractor 27, a second calculator 28, and a communication unit 29. The first amplifier 21 includes an amplifier 21a, an amplifier 21b, an amplifier 21c, and an amplifier 21d. The first calculator 23 includes a differential calculator 23a, a differential calculator 23b, a differential calculator 23c, and a differential calculator 23d.

Operations of the amplifier 21a, the amplifier 21b, the amplifier 21c, and the amplifier 21d, and operations of the differential calculator 23a, the differential calculator 23b, the differential calculator 23c, and the differential calculator 23d are similar. Therefore, description will be given using cases of the amplifier 21a and the differential calculator 23a as examples.

When having received a detection signal $S_{10a}$ from the first sensor 10a, the amplifier 21a amplifies the detection signal $S_{10a}$. The amplifier 21a then inputs the amplified detection signal $S_{10a}$ to the differential calculator 23a and the switch unit 24. Further, when having received a feedback signal that adjusts the degree of amplification of the detection signal $S_{10a}$ from the adjuster 26, the amplifier 21a adjusts the degree of amplification of the detection signal $S_{10a}$ based on the feedback signal. Hereinafter, for simplification, the amplified detection signal $S_{10a}$ is also simply referred to as detection signal $S_{10a}$.

Meanwhile, when having received a reference signal $S_{11}$ from the second sensor 11, the second amplifier 22 amplifies the reference signal $S_{11}$. The second amplifier 22 then inputs the amplified reference signal $S_{11}$ to the differential calculator 23a, the differential calculator 23b, the differential calculator 23c, and the differential calculator 23d. Further, when having received the feedback signal that adjusts the degree of amplification of the reference signal $S_{11}$ from the adjuster 26, the second amplifier 22 adjusts the degree of amplification of the reference signal $S_{11}$ based on the feedback signal. Hereinafter, for simplification, the amplified reference signal $S_{11}$ is also simply referred to as reference signal $S_{11}$.

When having received the detection signal $S_{10a}$ from the amplifier 21a, and the reference signal $S_{11}$ from the second amplifier 22, the differential calculator 23a calculates a difference detection signal $S_{10a}$-$S_{11}$ by subtracting the reference signal $S_{11}$ from the detection signal $S_{10a}$. Accordingly, the differential calculator 23a removes a noise component superimposed on the first sensor 10a and the second sensor 11 at the same phase. The differential calculator 23a inputs the difference detection signal $S_{10a}$-$S_{11}$ from which the noises have been canceled to the switch unit 24.

Similarly, the differential calculator 23b inputs a difference detection signal $S_{10b}$-$S_{11}$ from which the noises have been canceled to the switch unit 24. The differential calculator 23c inputs a difference detection signal $S_{10c}$-$S_{11}$ from which the noises have been canceled to the switch unit 24. The differential calculator 23d inputs a difference detection signal $S_{10d}$-$S_{11}$ from which the noises have been canceled to the switch unit 24.

Note that the second sensor 11 that outputs the reference signal $S_{11}$ also detects the elastic waves. Here, a method of not detecting the elastic waves as the reference signal by the second sensor will be described.

Figure 4:
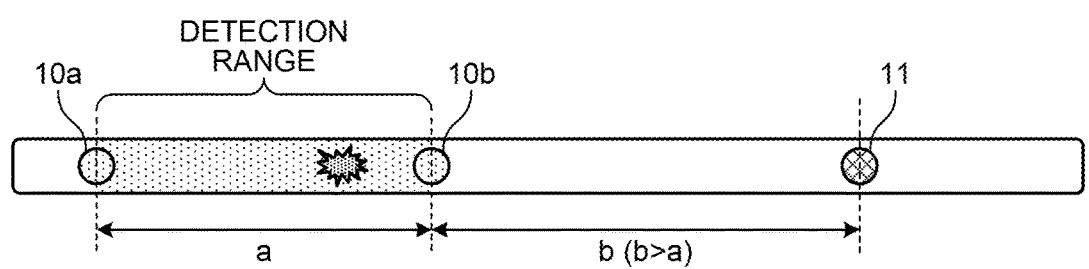
FIG. 4 is a diagram illustrating a first example of a positional relationship between a first sensor and a second sensor of an embodiment.

FIG. 4 is a diagram illustrating a first example of a positional relationship between the first sensor 10 and the second sensor 11. The example of FIG. 4 illustrates a case of installing the first sensor 10a, the first sensor 10b, and the second sensor 11 when the structure can be regarded as a one-dimensional object to be measured. A distance between the first sensor 10a and the first sensor 10b is a. In this case, the second sensor 11 is arranged in a position separated from the closest first sensor 10b by a distance b (b>a). Accordingly, the elastic wave generated from a measurement range first reaches first sensor 10a and the first sensor 10b, and then reaches the second sensor 11 with a sufficient time difference. Therefore, the positional relationship among the first sensor 10a, the first sensor 10b, and the second sensor 11 is set as illustrated in FIG. 4, so that the second sensor 11 can temporally separate the noises and the elastic wave.

Figure 5:
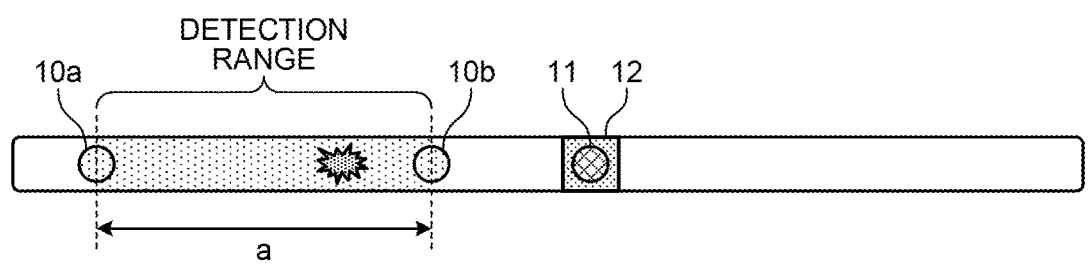
FIG. 5 is a diagram illustrating a second example of a positional relationship between the first sensor and the second sensor of an embodiment.

FIG. 5 is a diagram illustrating a second example of a positional relationship between the first sensor 10 and the second sensor 11. The example of FIG. 5 illustrates a case of not installing the second sensor 11 from installation positions of the first sensor 10a and the first sensor 10b with a sufficient distance. In this case, a silencing material 12 is installed between the second sensor 11 and an object to be measured, so that the elastic wave reaching the second sensor 11 is attenuated or reflected. The silencing material 12 is a material that attenuates the elastic wave or a material having different acoustic impedance from the object to be measured. The acoustic impedance is defined by a product of a sound speed in a medium and density, and is $46.4 \times 10^6$ [kg/m²s] in iron. In this case, as a material having acoustic impedance that is 10 times or more different from iron, for example, rubber ($1.5 \times 10^6$ [kg/m²s]), wood ($2 \times 10^6$ [kg/m²s]), acrylic ($3.3 \times 10^6$ [kg/m²s]), epoxy resin ($3 \times 10^6$ [kg/m²s]), water ($1.5 \times 10^6$ [kg/m²s]), air (428 [kg/m²s]), or the like can be used. The silencing material 12 is installed as illustrated in FIG. 5, so that the elastic wave cannot reach the second sensor 11. Therefore, the second sensor 11 can separate the noises and the elastic wave.

Figure 6:
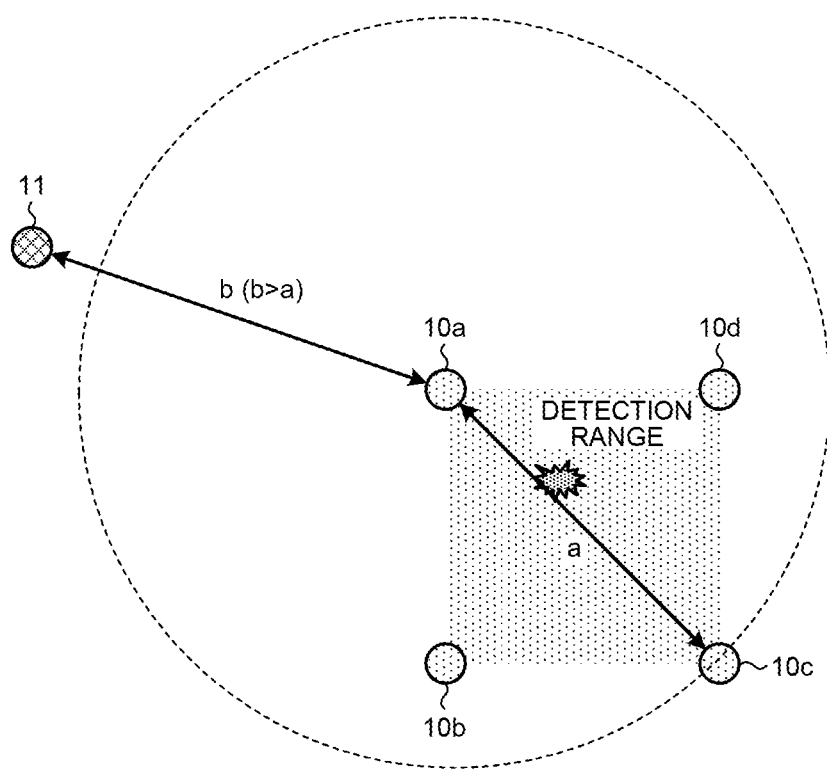
FIG. 6 is a diagram illustrating a first example of a positional relationship between the first sensor and the second sensor of an embodiment.

FIG. 6 is a diagram illustrating a first example of a positional relationship between the first sensor 10 and the second sensor 11. The example of FIG. 6 illustrates a case of installing the first sensor 10a, the first sensor 10b, the first sensor 10c, the first sensor 10d, and the second sensor 11 when the structure can be regarded as a two-dimensional object to be measured. When a maximum distance between the first sensors 10 is a, the maximum distance a is a distance between the first sensor 10a and the first sensor 10c (the first sensor 10b and the first sensor 10d). In this case, the second sensor 11 is arranged in a position separated from the closest first sensor 10a by a distance b (b>a). Accordingly, the elastic wave generated from the measurement range first reaches the four first sensors 10a to 10d, and then reaches the second sensor 11 with a sufficient time difference. Therefore, the positional relationship among the first sensor 10a, the first sensor 10b, the first sensor 10c, the first sensor 10d, and the second sensor 11 is set as illustrated in FIG. 6, whereby the second sensor 11 can temporally separate the noises and the elastic wave.

Figure 7:
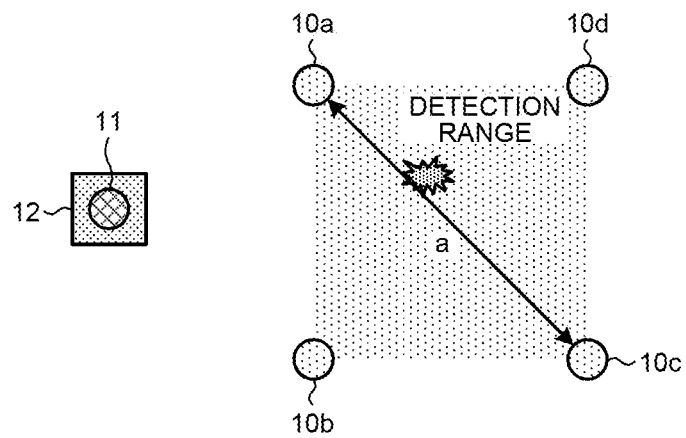
FIG. 7 is a diagram illustrating a second example of a positional relationship between the first sensor and the second sensor of an embodiment.

FIG. 7 is a diagram illustrating a second example of a positional relationship between the first sensor 10 and the second sensor 11. The example of FIG. 7 illustrates a case of not being able to install the second sensor 11 with a sufficient distance from installation positions of the first sensor 10a, the first sensor 10b, the first sensor 10c, and the first sensor 10d. Description of FIG. 7 is similar to the one dimensional case of FIG. 5, and is thus omitted.

Referring back to FIG. 1, the switch unit 24 includes a switch 24a, a switch 24b, a switch 24c, and a switch 24d.

The switch unit 24 inputs either the detection signal $S_{10a}$ or the difference detection signal $S_{10a}$-$S_{11}$ to the generator 25, the adjuster 26, and the extractor 27 through an AD converter (ADC) (not illustrated in FIG. 1) by switching the switch 24a.

When having received the detection signal $S_{10a}$ from which the noise component has been removed, the ADC quantizes and converts the detection signal $S_{10a}$ from which the noise component has been removed into a digital detection signal $S_{10a}$. The ADC inputs the digital detection signal $S_{10a}$ to the generator 25, the adjuster 26, and the extractor 27.

Similarly, the switch unit 24 inputs either the detection signal $S_{10b}$ or the difference detection signal $S_{10b}$-$S_{11}$ to the generator 25, the adjuster 26, and the extractor 27 through an ADC (not illustrated in FIG. 1) by switching the switch 24b. Further, the switch unit 24 inputs either the detection signal $S_{10c}$ or the difference detection signal $S_{10c}$-$S_{11}$ to the generator 25, the adjuster 26, and the extractor 27 through an ADC (not illustrated in FIG. 1) by switching the switch 24c. Further, the switch unit 24 inputs either the detection signal $S_{10d}$ or the difference detection signal $S_{10d}$-$S_{11}$ to the generator 25, the adjuster 26, and the extractor 27 through an ADC (not illustrated in FIG. 1) by switching the switch 24d.

To be specific, the generator 25 inputs, to the switch unit 24 and the extractor 27, a gate signal (selection signal) that switches the switch 24a (the switch 24b, the switch 24c, or the switch 24d) to an output of the difference detection signal $S_{10a}$-$S_{11}$ ($S_{10b}$-$S_{11}$, $S_{10c}$-$S_{11}$, or $S_{10d}$-$S_{11}$) until a predetermined time T passes, when any one of the detection signals $S_{10a}$ to $S_{10d}$ received from the switch unit 24 is a threshold (second threshold) or more. The predetermined time T is a processing time of the extractor 27. To be specific, the predetermined time T is a/v (a: a maximum distance between the first sensors 10, and v: a propagating speed of the elastic wave). Details of the processing of the extractor 27 will be described below.

Figure 8:
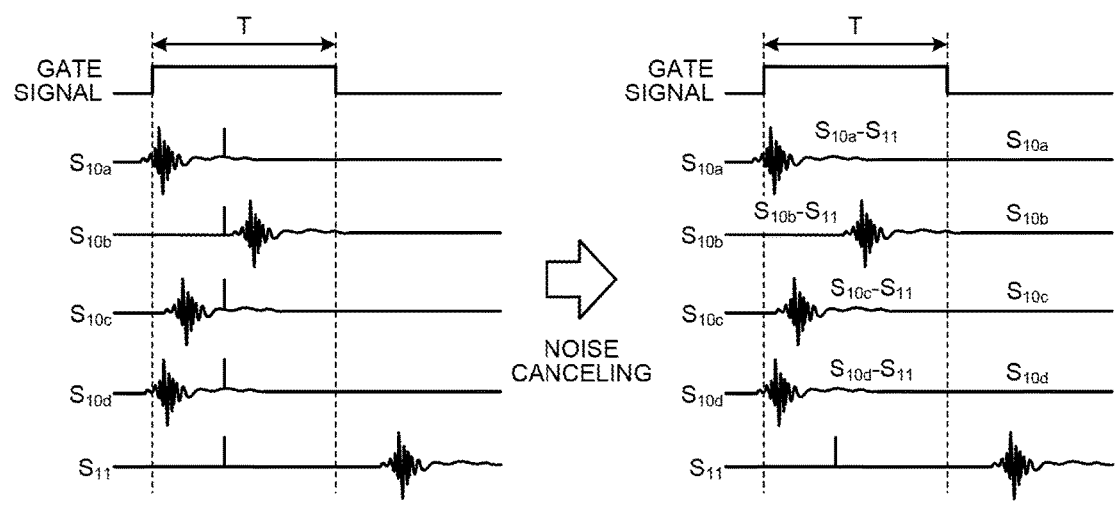
FIG. 8 is a conceptual diagram of noise canceling by a signal processing device of an embodiment.

FIG. 8 is a conceptual diagram of noise canceling by the signal processing device 20 of an embodiment. The example of FIG. 8 schematically illustrates outputs of the first sensors 10a to 10d, and the second sensor 11. When the elastic wave is generated from the structure, time differences according to the positions of the first sensors 10a to 10d and the second sensor 11 are caused at times when the first sensors 10a to 10d and the second sensor 11 detect the elastic wave. In the case of the example of FIG. 6, the time difference between the time when the first sensor 10a has first detected the elastic wave and the time when the second sensor 11 detects the elastic wave becomes at least a/v (a: a maximum distance between the first sensors 10 and v: a propagating speed of the elastic wave) or more. Meanwhile, the noises are superimposed on the first sensors 10a to 10d and the second sensor 11 at the same time.

Therefore, the first calculator 23 can cancel the noises by subtracting the reference signal $S_{11}$ from the second sensor 11, from the detection signals $S_{10a}$, $S_{10b}$, $S_{10c}$, and $S_{10d}$ from the first sensors 10a to 10d. Further, when the elastic wave has first reached the first sensor 10a, the first calculator 23 performs calculation processing within the range of the predetermined time T=a/v determined according to the installation positions of the first sensors 10a to 10d and the material of the structure, from the time when the first sensor 10a has detected the elastic wave, thereby to prevent the elastic wave leaked and transmitted to the second sensor 11 from being erroneously determined as a noise.

To be specific, the switch unit 24 switches the switch 24a (the switch 24b, the switch 24c, or the switch 24d) to an output of the difference detection signal $S_{10a}$-$S_{11}$ ($S_{10b}$-$S_{11}$, $S_{10c}$-$S_{11}$, or $S_{10d}$-$S_{11}$) by a gate signal that becomes Hi during the predetermined time T. Accordingly, the difference detection signals $S_{10a}$-$S_{11}$, $S_{10b}$-$S_{11}$, $S_{10c}$-$S_{11}$, and $S_{10d}$-$S_{11}$ are being input to the generator 25, the adjuster 26, and the extractor 27 until the predetermined time T passes. Note that the generator 25 does not perform the above-described threshold determination of switching the switch unit 24 while the gate signal is Hi.

Further, when the gate signal is changed from Hi to Lo due to the elapse of the predetermined time T, the switch unit 24 switches the switch 24a (the switch 24b, the switch 24c, or the switch 24d) to outputs of the detection signal $S_{10a}$ ($S_{10b}$, $S_{10c}$, or $S_{10d}$) again. Accordingly, the detection signals $S_{10a}$, $S_{10b}$, $S_{10c}$, and $S_{10d}$ are input to the generator 25 and the adjuster 26 again.

Figure 9A:
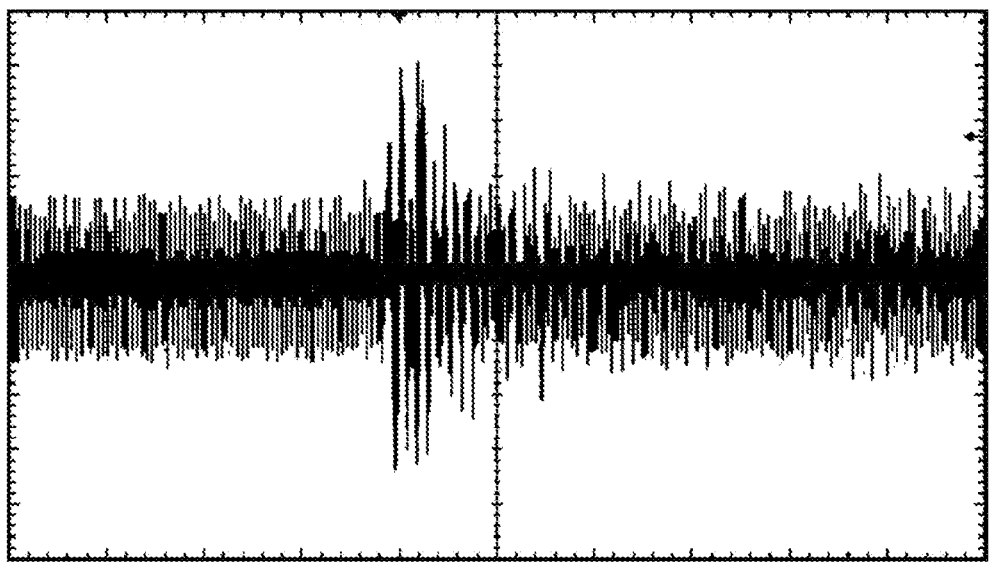
FIG. 9A is a diagram illustrating an example of a detection signal (with noises) of an embodiment.
Figure 9B:
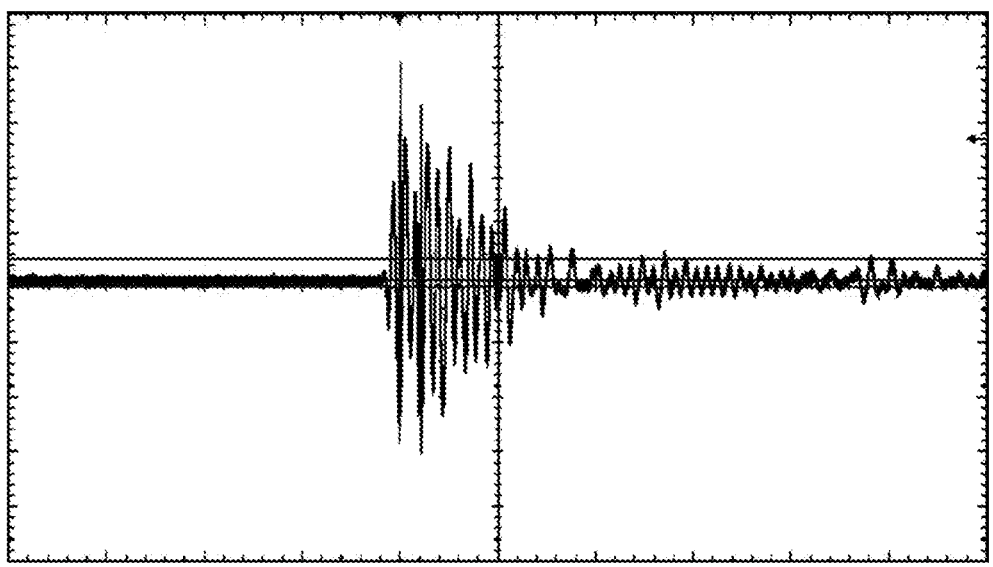
FIG. 9B is a diagram illustrating an example of a difference detection signal (without noises) of an embodiment.

FIG. 9A is a diagram illustrating an example of the detection signal $S_{10}$ (with noises) of an embodiment. Meanwhile, FIG. 9B is a diagram illustrating an example of the difference detection signal $S_{10}$-$S_{11}$ (without noises). As illustrated in FIG. 9B, in the difference detection signal $S_{10}$-$S_{11}$, the noises included in the detection signal $S_{10}$ are canceled.

Referring back to FIG. 1, further, when having received the detection signal $S_{10a}$ ($S_{10b}$, $S_{10c}$, or $S_{10d}$), or the difference detection signal $S_{10a}$-$S_{11}$ ($S_{10b}$-$S_{11}$, $S_{10c}$-$S_{11}$, or $S_{10d}$-$S_{11}$) from the switch unit 24, the adjuster 26 adjusts the degree of amplification of the first amplifier 21 or the second amplifier 22 based on the detection signal $S_{10a}$ ($S_{10b}$, $S_{10c}$, or $S_{10d}$), or the difference detection signal $S_{10a}$-$S_{11}$ ($S_{10b}$-$S_{11}$, $S_{10c}$-$S_{11}$, or $S_{10d}$-$S_{11}$). When adjusting the degree of amplification of the detection signal $S_{10a}$ ($S_{10b}$, $S_{10c}$, or $S_{10d}$), the adjuster 26 inputs the feedback signal that adjusts the degree of amplification of the detection signal $S_{10a}$ ($S_{10b}$, $S_{10c}$, or $S_{10d}$) to the amplifier 21a (21b, 21c, or 21d). When adjusting the degree of amplification of the reference signal $S_{11}$, the adjuster 26 inputs the feedback signal that adjusts the degree of amplification of the reference signal $S_{11}$ to the second amplifier 22.

When the gate signal input from the generator 25 is Hi, the extractor 27 receives the difference detection signals $S_{10a}$-$S_{11}$ to $S_{10d}$-$S_{11}$ from the switch unit 24. The extractor 27 stores the time information that indicates the times when the extractor 27 has received the respective difference detection signals $S_{10a}$-$S_{11}$ to $S_{10d}$-$S_{11}$. The extractor 27 extracts the feature amount information from the respective difference detection signals $S_{10a}$-$S_{11}$ to $S_{10d}$-$S_{11}$. The respective pieces of feature amount information of the difference detection signals $S_{10a}$-$S_{11}$ to $S_{10d}$-$S_{11}$ are similar, and thus a case of the difference detection signal $S_{10a}$-$S_{11}$ will be described as an example.

The feature amount information of the difference detection signal $S_{10a}$-$S_{11}$ exhibits the feature of the difference detection signal $S_{10a}$-$S_{11}$. The feature amount information of the difference detection signal $S_{10a}$-$S_{11}$ is, for example, an amplitude [mV] of a waveform of the difference detection signal $S_{10a}$-$S_{11}$, a duration [μsec] of the waveform of the difference detection signal $S_{10a}$-$S_{11}$, the number of zero cross counts [times] of the difference detection signal $S_{10a}$-$S_{11}$, energy [arb.] of the waveform of the difference detection signal $S_{10a}$-$S_{11}$, and a frequency [Hz] of the difference detection signal $S_{10a}$-$S_{11}$.

The extractor 27 inputs the respective pieces of feature amount information and time information of the difference detection signals $S_{10a}$-$S_{11}$ to $S_{10a}$-$S_{11}$ to the second calculator 28.

The second calculator 28 receives the respective pieces of feature amount information and time information of the difference detection signals $S_{10a}$-$S_{11}$ to $S_{10d}$-$S_{11}$ from the extractor 27. The second calculator 28 divides the plurality of difference detection signals $S_{10a}$-$S_{11}$ to $S_{10a}$-$S_{11}$ into groups based on whether the similarities of the feature amount information of the difference detection signals $S_{10a}$-$S_{11}$ to $S_{10a}$-$S_{11}$ are a predetermined threshold (first threshold) or more. Then, the second calculator 28 recognizes the difference detection signals $S_{10a}$-$S_{11}$ to $S_{10a}$-$S_{11}$ included in the same group as the difference detection signals $S_{10a}$-$S_{11}$ to $S_{10d}$-$S_{11}$ of the same generation source.

Note that the similarity is determined according to a distance between the feature amount information and the feature amount information. That is, the similarity is larger as the distance between different pieces of the feature amount information is closer. The second calculator 28 calculates the distance between the pieces of feature amount information by a predetermined distance function. The distance function is a function for calculating, for example, a standard Euclidean distance, a Minkowski distance, or a Mahalanobis distance. Especially, the Mahalanobis distance enables calculation of the distance, considering correlation between the pieces of feature amount information, and can improve classification accuracy of the groups.

The second calculator 28 calculates time difference information from the time information of the difference detection signals $S_{10a}$-$S_{11}$ to $S_{10d}$-$S_{11}$ corresponding to the feature amount information with the similarity being a predetermined threshold or more (the feature amount information of the difference detection signals $S_{10a}$-$S_{11}$ to $S_{10d}$-$S_{11}$ included in the same group). The second calculator 28 calculates positional information of the generation source of the elastic wave based on the positional information of the first sensors 10a to 10d, the time difference information, and the propagating speed of the elastic wave. Here, the propagating speed of the elastic wave will be described.

The propagation speed v of the elastic wave propagating in a material is expressed by the following Equation (1), using elastic modulus K [Pa] of the material and density $\rho_0$ [kg/m³].

$$v = \sqrt{\frac{K}{\rho_0}} \quad (1)$$

Further, the propagating speed v of the elastic wave propagating in a structure (three-dimensional body) is expressed by the following Equation (2), in consideration of shearing modulus G of the material.

$$v = \sqrt{\frac{1}{\rho_0} \cdot \left(K + \frac{4}{3}G\right)} \quad (2)$$

That is, the propagating speed of the elastic wave is determined according to physical properties unique to the material. Therefore, the propagation speed information calculated in advance for each material (the quality of the material of the structure) is stored by the second calculator 28 as a look-up table, for example, so that an appropriate propagating speed according to the quality of the material of the structure can be selected from the look-up table.

Figures 10, 11:
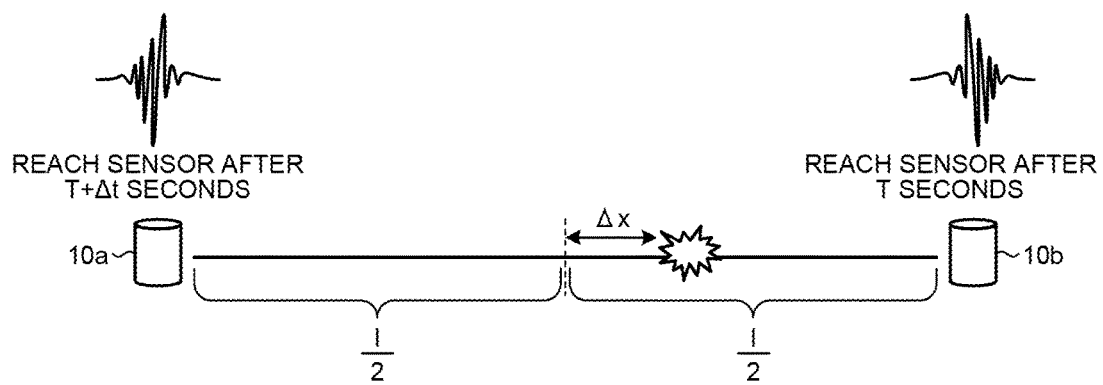
FIG. 10 is a diagram illustrating an example of propagating speed information of an embodiment.
FIG. 11 is a diagram for describing an example of a position calculation method of an embodiment (in a case of one dimension)

FIG. 10 is a diagram illustrating an example of propagating speed information of an embodiment. FIG. 10 illustrates an example of a case of storing the propagating speed information as a look-up table. For example, the propagating speed v of when the quality of the material of the structure is iron is 5950 [m/s].

Next, a method of calculating the position of the generation source of the elastic wave by the second calculator 28 will be described. For simplification, a case of one dimension will be described in detail. Note that cases of two dimensions and three dimensions have the same principle.

FIG. 11 is a diagram for describing an example of a position calculation method of an embodiment (in a case of one dimension). A case in which a crack of the structure is cased between the first sensor 10a and the first sensor 10b, and the elastic wave due to the crack is detected by the first sensor 10a and the first sensor 10b will be described.

A distance between the first sensor 10a and the first sensor 10b is 1. Further, a distance from an intermediate point of the first sensor 10a and the first sensor 10b to the crack is Δx. At this time, when the first sensor 10b detects the elastic wave after T seconds, and the first sensor 10a detects the elastic wave after T+Δt seconds, the time difference information Δt can be expressed by the following Equation (3).

$$\Delta t = \left(\left(\frac{1}{2}+\Delta x\right)-\left(\frac{1}{2}-\Delta x\right)\right)/v = 2\Delta x/v \quad (3)$$

Therefore, if the distance l between the first sensor 10a and the first sensor 10b and the propagating speed v of the elastic wave are known, the second calculator 28 can calculate the distance Δx from the intermediate point of the first sensor 10a and the first sensor 10b to the crack from Equation (3) by calculating the time difference information Δt. That is, the second calculator 28 can calculate the positional information of the crack (generation source of the elastic wave) from the time difference information Δt.

Figure 12:
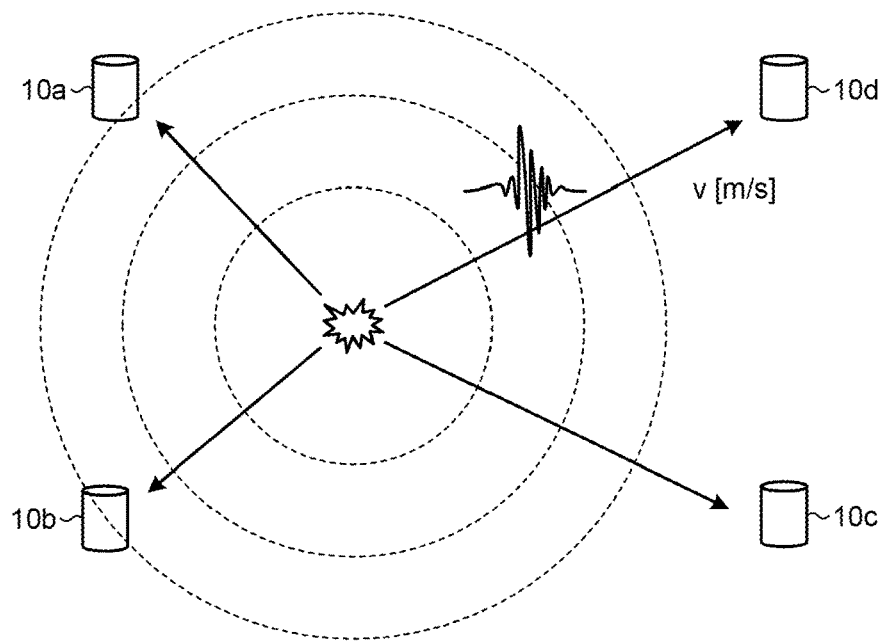
FIG. 12 is a diagram for describing an example of a position calculation method of an embodiment (in a case of two dimensions)
Figure 13:
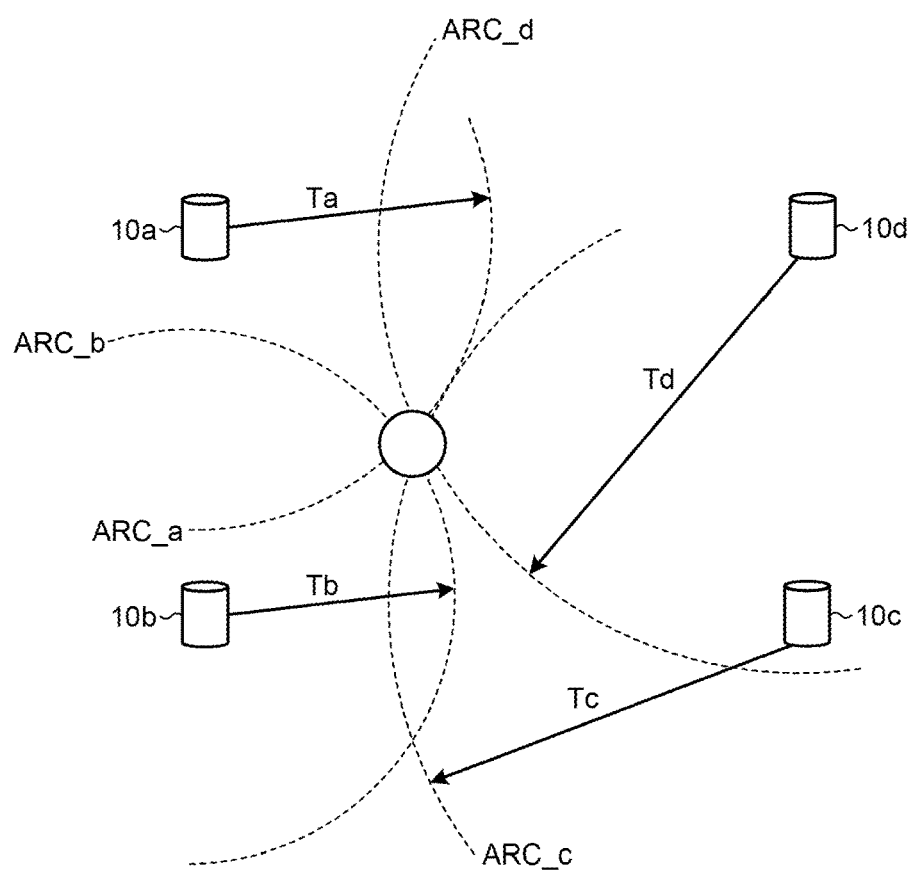
FIG. 13 is a diagram for describing an example of a position calculation method of an embodiment (in a case of two dimensions)

Next, a case of two dimensions will be briefly described. FIGS. 12 and 13 are diagrams for describing an example of a position calculation method of an embodiment (a case of two dimensions). FIG. 12 illustrates a case in which a crack is caused in the structure, and the elastic wave due to the crack reaches the first sensors 10a to 10d at the propagating speed v [m/s]. Times when the elastic wave reaches the respective first sensors 10a to 10d are different among the first sensors 10a to 10d. If time differences among receiving times of the elastic wave can be known, the generation source of the elastic wave can be estimated to be positioned on a circumference ARC_a (radius Ta), a circumference ARC_b (radius Tb), a circumference ARC_c (radius Tc), and a circumference ARC_d (radius Td) having the respective first sensors 10a to 10d as the centers, as illustrated in FIG. 13. That is, the second calculator 28 can calculate an intersection point of the circumferences ARC_a to ARC_d as the positional information of the generation source of the elastic wave.

Typically, by use of (the number of dimensions+1) first sensors 10, the position of the generation source of the elastic wave can be calculated. Therefore, in a case of three dimensions, by use of four first sensors 10, the position of the generation source of the elastic wave can be calculated. Further, calculation accuracy of the positional information can be further improved as the number of the first sensors 10 is larger.

Referring back to FIG. 1, when the calculated positional information falls outside a predetermined measurement range (does not satisfy a predetermined threshold), the second calculator 28 performs noise processing of removing the feature amount information of the difference detection signals $S_{10a}$-$S_{11}$ to $S_{10d}$-$S_{11}$ used for the calculation as noises. The second calculator 28 inputs the feature amount information and the positional information to the communication unit 29.

When having received the feature amount information and the positional information from the second calculator 28, the communication unit 29 transmits the feature amount information and the positional information to the server device 50.

When having received the feature amount information and the positional information from the signal processing device 20, the server device 50 performs processing based on the feature amount information and the positional information.

Figure 14:
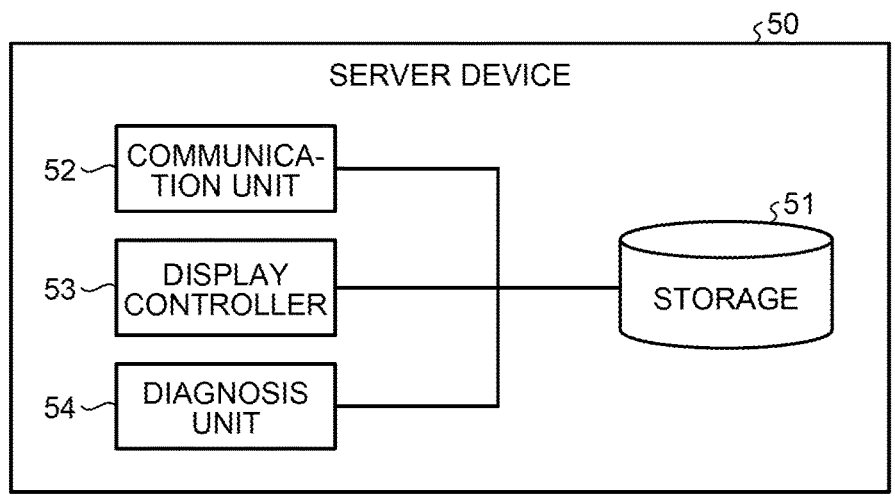
FIG. 14 is a diagram illustrating an example of a functional configuration of a server device of an embodiment.

FIG. 14 is a diagram illustrating an example of a functional configuration of the server device 50 of an embodiment. The server device 50 of an embodiment includes a storage 51, a communication unit 52, a display controller 53, and a diagnosis unit 54.

The storage 51 stores information. The information stored in the storage 51 is the feature amount information and the positional information acquired in the signal processing device 20, for example.

When having received the feature amount information and the positional information from the signal processing device 20, the communication unit 52 stores the feature amount information and the positional information in the storage 51. The display controller 53 performs display control based on the feature amount information and the positional information stored in the storage 51. The diagnosis unit 54 diagnoses the degree of deterioration of the structure based on the feature amount information and the positional information stored in the storage 51. When there is a place where total energy of the elastic wave becomes predetermined energy or more, the diagnosis unit 54 performs display of a warning that indicates a risk of deterioration in the place, to the display controller 53.

Figure 15:
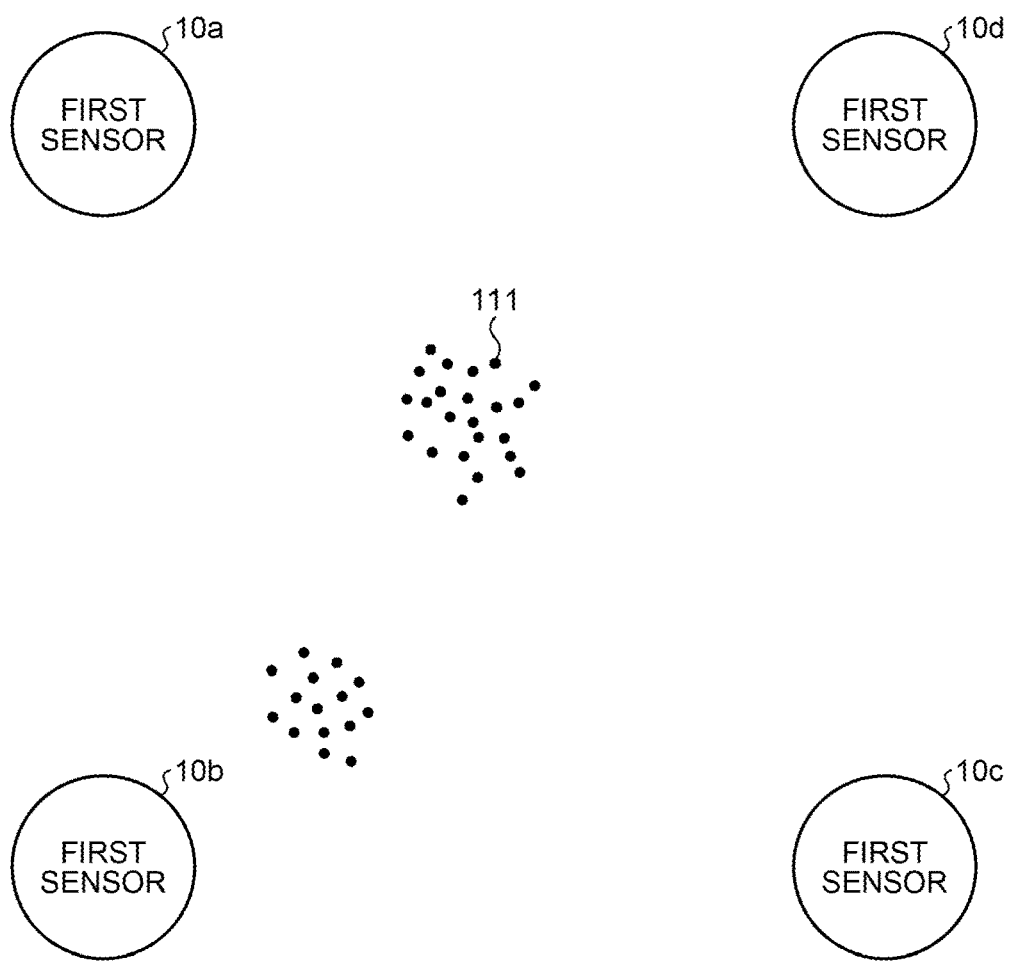
FIG. 15 is a diagram illustrating an example of display information indicating positional information of an embodiment.

FIG. 15 is a diagram illustrating an example of display information that indicates the positional information of an embodiment. FIG. 15 illustrates an example of a case of displaying the generation source of the elastic wave with positional information 111 and the like.

Figure 16:
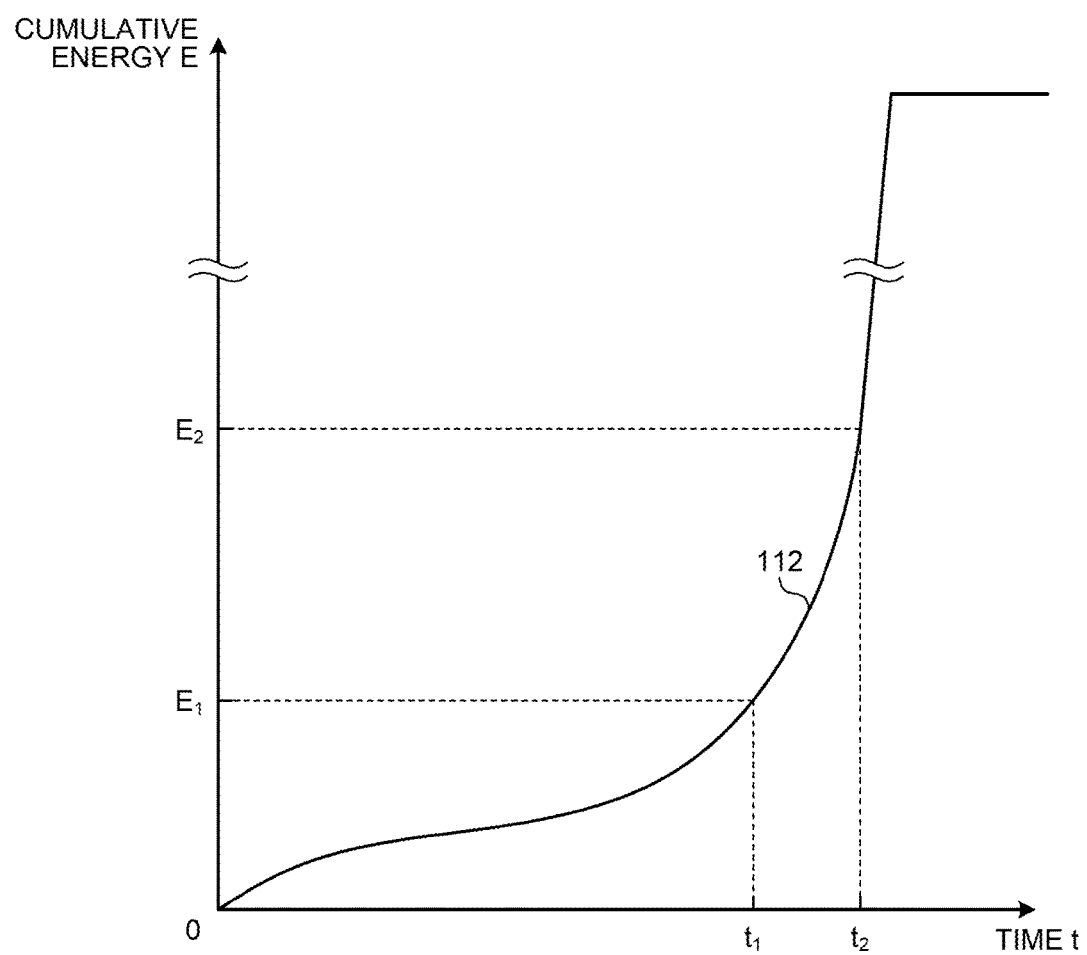
FIG. 16 is a diagram illustrating an example of display information indicating cumulative energy of an embodiment.

FIG. 16 is a diagram illustrating an example of the display information that indicates cumulative energy of an embodiment. FIG. 16 illustrates a case of displaying the cumulative energy by a curved line 112. The display controller 53 performs control of displaying the display information illustrated in FIG. 16, for example, when there is an input that indicates selection of the positional information 111 when the display information illustrated in FIG. 15 is being displayed. Further, when a user specifies a selection range on a screen where the display information illustrated in FIG. 15 is displayed, the cumulative energy of the elastic wave included in the selection range is displayed by the curved line 112, whereby a feature can be more easily grasped. The selection range is, for example, an inside of a square with a diagonal line from a dragged position to a dropped position specified by a drag-and-drop operation of a mouse, or an inside of a circle inscribed in the square, whereby operability can be further improved.

In FIG. 16, $E_1$ is a threshold used when the state of the deterioration of the structure is diagnosed by the diagnosis unit 54. That is, the diagnosis unit 54 requests the display controller 53 to display a warning or the like that indicates that the degree of deterioration is large at a time $t_1$ when a value of the cumulative energy becomes $E_1$. Accordingly, an administrator of the structure or the like can grasp a high possibility of causing a rupture of the structure before the rupture of the structure is caused due to further development of the deterioration. Note that the example of FIG. 16 indicates a case in which the rupture of the structure is caused at a time $t_2$. At and after the cumulative energy $E_2$, the cumulative energy E is sharply increased due to impact at the time of the rupture of the structure. Then, when the state of the structure becomes stable after the rupture, the elastic wave is not generated, and the cumulative energy E becomes constant.

Next, a detection method of an embodiment will be described.

Figure 17:
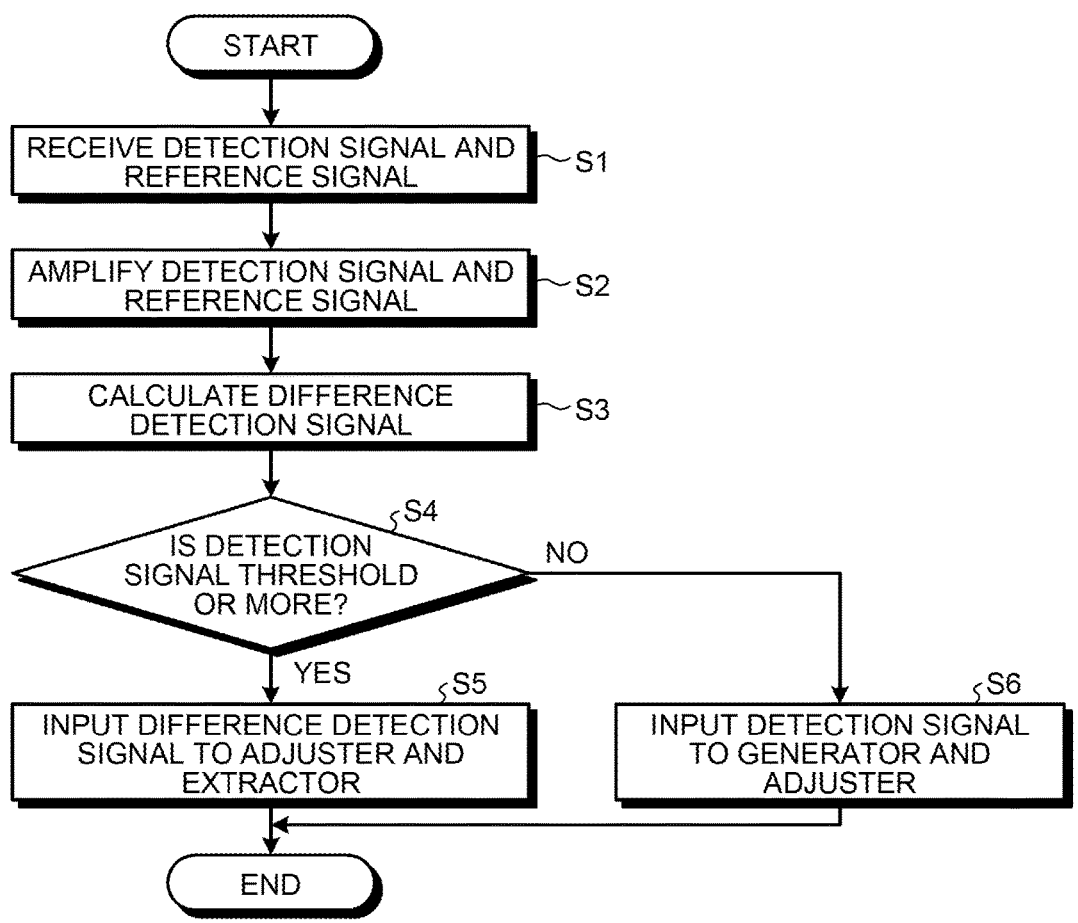
FIG. 17 is a flowchart illustrating an example of a detection method (signal selection processing) of an embodiment.

FIG. 17 is a flowchart illustrating an example of a detection method (signal selection processing) of an embodiment. First, the first amplifier 21 receives the detection signal $S_{10}$ from the first sensor 10, and the second amplifier 22 receives the reference signal $S_{11}$ from the second sensor 11 (step S1). Next, the first amplifier 21 amplifies the detection signal $S_{10}$, and the second amplifier 22 amplifies the reference signal $S_{11}$ (step S2). Next, the first calculator 23 calculates the difference detection signal $S_{10}$-$S_{11}$ by subtracting the reference signal $S_{11}$ from the detection signal $S_{10}$ (step S3).

Next, the generator 25 determines whether any one of the detection signals $S_{10a}$ to $S_{10d}$ is a threshold or more (step S4).

When any one of the detection signals is the threshold or more (Yes in step S4), the switch 24a (the switch 24b, the switch 24c, or the switch 24d) inputs the difference detection signal $S_{10a}$-$S_{11}$ ($S_{10b}$-$S_{11}$, $S_{10c}$-$S_{11}$, or $S_{10d}$-$S_{11}$) to the adjuster 26 and the extractor 27 until the predetermined time T passes (step S5).

When all the detection signals Snare less than the threshold (No in step S4), the switch 24a (the switch 24b, the switch 24c, or the switch 24d) inputs the detection signal $S_{10}$a ($S_{10b}$, $S_{10c}$, or $S_{10d}$) to the generator 25 and the adjuster 26 (step S6).

Figure 18:
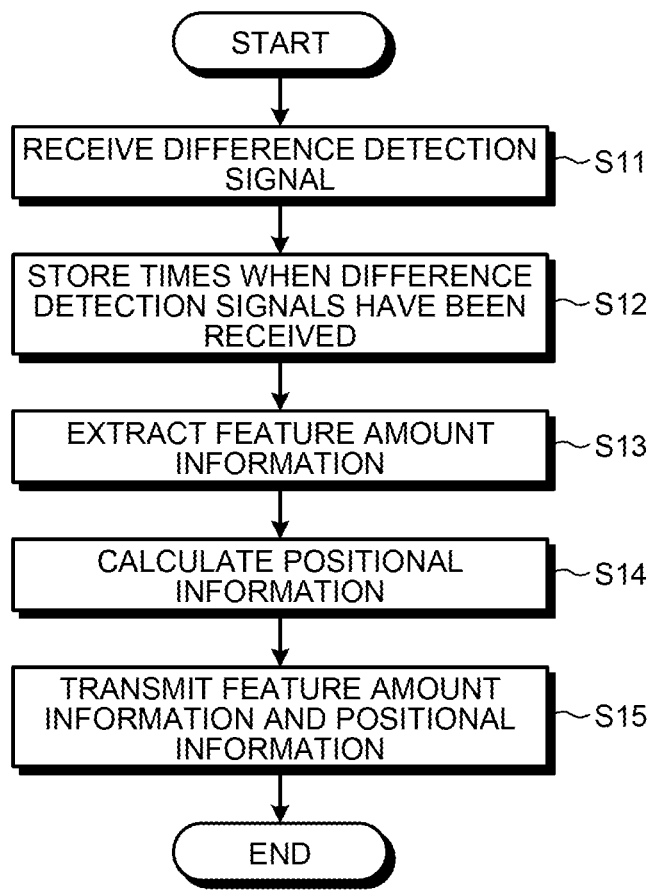
FIG. 18 is a flowchart illustrating an example of a detection method (position information calculation processing) of an embodiment.

FIG. 18 is a flowchart illustrating an example of a detection method (positional information calculation processing) of an embodiment. First, the extractor 27 receives the difference detection signals $S_{10a}$-$S_{11}$ to $S_{10d}$-$S_{11}$ from the switch unit 24 (step S11). Next, the extractor 27 stores the time information that indicates the times when the extractor 27 has received the respective difference detection signals $S_{10a}$-$S_{11}$ to $S_{10d}$-$S_{11}$ (step S12). Next, the extractor 27 extracts the feature amount information from the respective difference detection signals $S_{10a}$-$S_{11}$ to $S_{10d}$-$S_{11}$ (step S13).

Next, the second calculator 28 calculates the positional information that indicates the position of the generation source of the elastic wave from the time information stored in step S12 and the feature amount information extracted in step S13 (step S14). To be specific, the second calculator 28 divides the plurality of difference detection signals $S_{10a}$-$S_{11}$ to $S_{10d}$-$S_{11}$ into groups based on whether the similarities of the feature amount information of the difference detection signals $S_{10a}$-$S_{11}$ to $S_{10d}$-$S_{11}$ a predetermined threshold or more. Next, the second calculator 28 recognizes the difference detection signals $S_{10a}$-$S_{11}$ to $S_{10d}$-$S_{11}$ included in the same group as the difference detection signals $S_{10a}$-$S_{11}$ to $S_{10d}$-$S_{11}$ of the same generation source. Next, the second calculator 28 calculates the time difference information from the time information of the difference detection signals $S_{10a}$-$S_{11}$ to $S_{10d}$-$S_{11}$ corresponding to the feature amount information with the similarity being the predetermined threshold or more (the feature amount information of the detection information included in the same group). Next, the second calculator 28 calculates the positional information that indicates the positional information of the generation source of the elastic wave from the time difference information, and the propagating speed v of the elastic wave according to the quality of the material of the structure.

Next, the communication unit 29 transmits the feature amount information extracted in step S12 and the positional information calculated in step S13 to the server device 50 (step S15).

Figure 19:
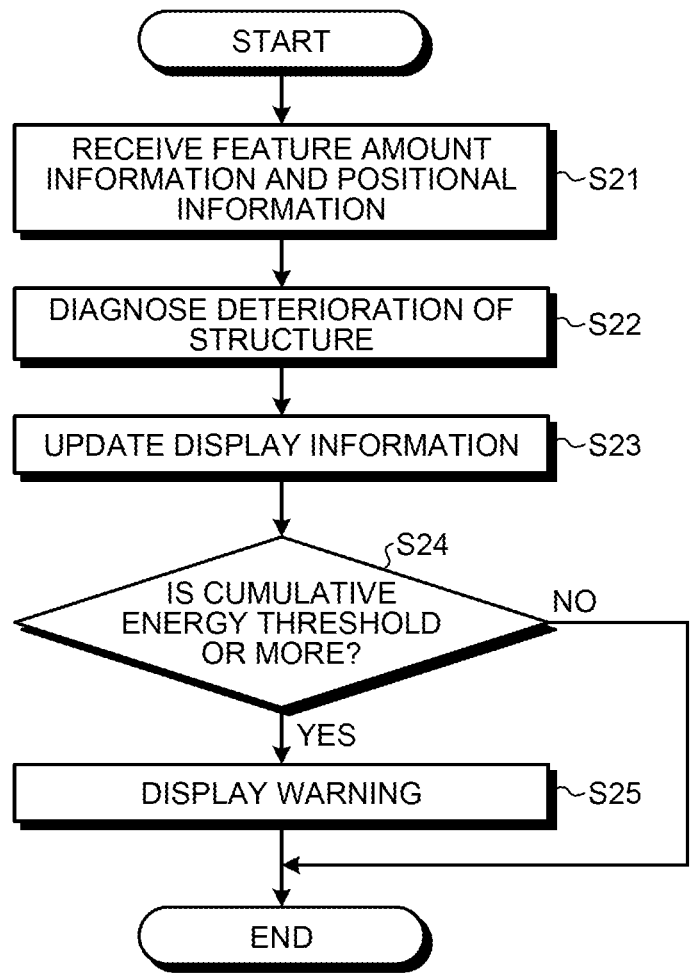
FIG. 19 is a flowchart illustrating an example of a detection method (display processing) of an embodiment.

FIG. 19 is a flowchart illustrating an example of a detection method (display processing) of an embodiment. First, the communication unit 52 receives the feature amount information and the positional information from the signal processing device 20 (step S21).

Next, the diagnosis unit 54 diagnoses deterioration of the structure based on the feature amount information and the positional information (step S22). To be specific, the diagnosis unit 54 diagnoses the deterioration of the structure by determining whether there is a generation source where the cumulative energy of the elastic wave becomes a predetermined threshold or more.

Next, the display controller 53 updates the display information to be displayed in the display device based on the feature amount information and the positional information, and a diagnosis result obtained by the processing of step S22 (step S23). The display information is, for example, the information of FIGS. 15 and 16, and the like.

Next, when the cumulative energy is the threshold or more (Yes in step S24), the display controller 53 displays a warning indicating that the degree of deterioration of the structure is large in the display device (step S25). When the cumulative energy is less than the threshold (No in step S24), the processing is terminated.

Finally, an example of a hardware configuration of the server device 50 of an embodiment will be described.

Figure 20:
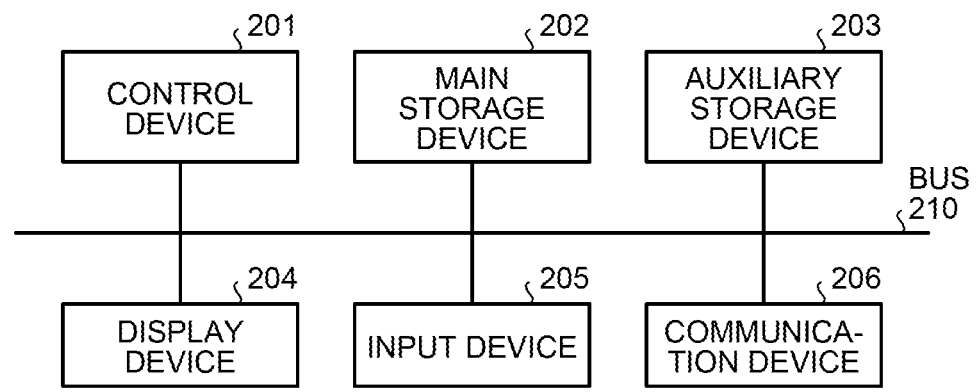
FIG. 20 is a diagram illustrating an example of a hardware configuration of a server device of an embodiment.

FIG. 20 is a diagram illustrating an example of a hardware configuration of the server device 50 of an embodiment. The server device 50 of an embodiment includes a control device 201, a main storage device 202, an auxiliary storage device 203, a display device 204, an input device 205, and a communication device 206. The control device 201, the main storage device 202, the auxiliary storage device 203, the display device 204, the input device 205, and the communication device 206 are connected through a bus 210. The server device 50 is, for example, a personal computer, a smart device, and the like.

The control device 201 executes a program read by the main storage device 202 from the auxiliary storage device 203. The main storage device 202 is memories such as a read only memory (ROM) and a random access memory (RAM). The auxiliary storage device 203 is a hard disk drive (HDD), a memory card, and the like. The storage 51 of FIG. 14 corresponds to the main storage device 202 and the auxiliary storage device 203.

The display device 204 displays a state of the server device 50, and the like. The display device 204 is a liquid crystal display, for example. The input device 205 is an interface for operating the server device 50. The input device 205 is, for example, a keyboard, a mouse, and the like. When the server device 50 is the smart device such as a smart phone and a tablet terminal, the display device 204 and the input device 205 are a touch panel, for example. The communication device 206 is an interface for being connected to a network.

The program executed in the server device 50 of an embodiment is recorded in storage media readable by a computer, such as a CD-ROM, a memory card, a CD-R, and a digital versatile disk (DVD) in an installable format file or an executable format file, and is provided as a computer program product.

Further, the program executed in the server device 50 of an embodiment may be stored on a computer connected to a network such as the Internet, and provided by being downloaded through the network. Further, the program executed in the server device 50 of an embodiment may be provided through the network such as the Internet without being downloaded.

Further, the program of the server device 50 of an embodiment may be provided by being incorporated in a ROM or the like in advance.

The program executed in the server device 50 of an embodiment is a module configuration including the function blocks (the communication unit 52, the display controller 53, and the diagnosis unit 54) of FIG. 14. As actual hardware of the function blocks, the program is read from the storage medium and executed by the control device 201, so that the function blocks are loaded onto the main storage device 202. That is, the function blocks are generated on the main storage device 202. Note that a part or all of the function blocks of FIG. 14 may be realized by hardware such as an integrated circuit (IC) instead of being realized by software.

As described above, in the detection system 1 of an embodiment, the plurality of first sensors 10 detects the elastic wave generated from the structure, and converts the elastic wave into the detection signal $S_{10}$. Further, the second sensor 11 detects the noises propagating from surroundings, and converts the noises into the reference signal $S_{11}$. Further, the first calculator 23 calculates the plurality of difference detection signals $S_{10}$-$S_{11}$ based on the respective detection signals $S_{10}$ and the reference signal $S_{11}$. The second calculator 28 then calculates the position of the generation source of the elastic wave from the plurality of difference detection signals $S_{10}$-$S_{11}$. Accordingly, according to the detection system 1 of an embodiment, the elastic wave can be highly accurately detected without depending on a detection environment of the elastic wave.

Note that, in the description of the detection system 1, configurations of the function blocks included in the respective devices may be changed. For example, the second calculator 28 of the signal processing device 20 may be realized in the server device 50. The second calculator 28 is realized in the server device 50, so that when the calculated positional information is outside the predetermined measurement range (when the calculated positional information does not satisfy the predetermined threshold), a condition of the threshold used for determination of the noise processing of removing the feature amount information of the difference detection signals $S_{10a}$-$S_{11}$ to $S_{10d}$-$S_{11}$ used for the calculation as noises can be flexibly changed. That is, deviation of the installation position of the first sensor 10, a condition of the structure to be measured, a weather condition, and the like can be flexibly changed. Therefore, the second calculator 28 can more effectively remove the noises.

Further, in this case, non-calculation of the positional information in the signal processing device 20 can reduce the power consumption of the signal processing device 20. Accordingly, the signal processing device 20 can be operated by a solar battery, a vibration power generation module, and the like, whereby the signal processing device 20 can be installed in a place with no power supply.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A detection system comprising:
   a plurality of first sensors each configured to detect an elastic wave generated from a structure, and convert the elastic wave into a detection signal;
   a second sensor configured to detect a noise propagating from surroundings, and convert the noise into a reference signal;
   a first calculator configured to calculate a plurality of difference detection signals based on the respective detection signals, each difference detection signal being calculated by subtracting the reference signal from the detection signal; and
   a second calculator configured to calculate a position of a generation source of the elastic wave from the plurality of difference detection signals, wherein
      a distance b between the second sensor and the first sensor closest to the second sensor is larger than a distance a between the closest first sensor and the first sensor farthest from the closest first sensor, and
      the first calculator cancels, without subtracting the reference signal from the detection signal, the reference signal that is obtained after a time obtained by dividing the distance a by a speed of the elastic wave, the time starting when the elastic wave first reached any one of the plurality of first sensors.

2. The system according to claim 1, wherein the first calculator performs calculation to calculate the plurality of difference detection signals within a range of a time obtained by dividing a maximum distance between the first sensors by the speed of the elastic wave when the elastic wave has first reached any one of the first sensors.

3. The system according to claim 1, wherein the second sensor is installed in the structure through a silencing material that attenuates or reflects the elastic wave reaching the second sensor.

4. The system according to claim 1, further comprising:
   a first amplifier configured to amplify the detection signal input from the first sensor, and input the amplified detection signal to the first calculator; and
   a second amplifier configured to amplify the reference signal input from the second sensor, and input the amplified reference signal to the first calculator.

5. The system according to claim 4, further comprising an adjuster configured to receive the detection signal or the difference detection signal, and adjust the degrees of amplification of the first amplifier and the second amplifier based on the detection signal or the difference detection signal.

6. The system according to claim 1, further comprising an extractor configured to extract feature amount information indicating a feature of each difference detection signal from the each difference detection signal,
   wherein the second calculator calculates a similarity of the feature amount information, and calculates the position of the generation source of the elastic wave based on time difference information indicating a time difference between times when the difference detection signals from which the feature amount information having the similarity being a first threshold or more has been extracted have been received, positional information indicating positions of the plurality of first sensors, and a propagating speed of the elastic wave.

7. The system according to claim 6, wherein the feature amount information includes at least one of an amplitude of a waveform of the difference detection signal, a duration of the waveform of the difference detection signal, the number of zero cross counts of the difference detection signal, energy of the waveform of the difference detection signal, and a frequency of the difference detection signal.

8. The system according to claim 7, further comprising:
   a switch unit configured to select either the detection signal or the difference detection signal according to a selection signal; and
   a generator configured to generate the selection signal indicating that the difference detection signal is being selected until a predetermined time passes when the detection signal received from the switch unit is a second threshold or more, wherein the extractor receives the difference detection signal from the switch unit.

9. A detection method comprising:

detecting, by each of a plurality of first sensors, an elastic wave generated from a structure to convert the elastic wave into a detection signal;

detecting, by a second sensor, a noise propagating from surroundings to convert the noise into a reference signal;

calculating, by a first calculator, a plurality of difference detection signals, each difference detection signal being calculated by subtracting the reference signal from the detection signal; and calculating, by a second calculator, a position of a generation source of the elastic wave from the plurality of difference detection signals, wherein a distance b between the second sensor and the first sensor closest to the second sensor is larger than a distance a between the closest first sensor and the first sensor farthest from the closest first sensor, and the calculating by the first calculator cancels, without subtracting the reference signal from the detection signal, the reference signal that is obtained after a time obtained by dividing the distance a by a speed of the elastic wave, the time starting when the elastic wave first reached any one of the plurality of first sensors.

* * * * *